(12) United States Patent
Burkhart

(10) Patent No.: US 11,839,369 B2
(45) Date of Patent: *Dec. 12, 2023

(54) SURGICAL CONSTRUCTS AND METHODS OF TISSUE REPAIR

(71) Applicant: Arthrex, Inc., Naples, FL (US)

(72) Inventor: Stephen S Burkhart, Boerne, TX (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/942,451

(22) Filed: Sep. 12, 2022

(65) Prior Publication Data

US 2023/0000485 A1  Jan. 5, 2023

Related U.S. Application Data

(63) Continuation of application No. 16/419,801, filed on May 22, 2019, now Pat. No. 11,439,382, which is a continuation of application No. 14/918,401, filed on Oct. 20, 2015, now Pat. No. 10,368,855.

(51) Int. Cl.
*A61B 17/04* (2006.01)
*A61B 17/00* (2006.01)
*A61B 17/06* (2006.01)

(52) U.S. Cl.
CPC ...... *A61B 17/0401* (2013.01); *A61B 17/0485* (2013.01); *A61B 2017/00004* (2013.01); *A61B 2017/044* (2013.01); *A61B 2017/045* (2013.01); *A61B 2017/0409* (2013.01); *A61B 2017/0412* (2013.01); *A61B 2017/0414* (2013.01); *A61B 2017/0445* (2013.01); *A61B 2017/0454* (2013.01); *A61B 2017/0458* (2013.01); *A61B 2017/0464* (2013.01); *A61B 2017/06185* (2013.01)

(58) Field of Classification Search
None
See application file for complete search history.

(56) References Cited

U.S. PATENT DOCUMENTS

| | | |
|---|---|---|
| 6,666,877 B2 | 12/2003 | Morgan |
| 6,716,234 B2 | 4/2004 | Grafton et al. |
| 7,329,272 B2 | 2/2008 | Burkhart et al. |
| 8,197,511 B2 | 6/2012 | Miller |
| 8,298,262 B2 | 10/2012 | Stone |
| 8,439,976 B2 | 5/2013 | Albertorio et al. |
| 8,460,379 B2 | 6/2013 | Albertorio et al. |
| 8,771,315 B2 | 7/2014 | Lunn |
| 9,005,246 B2 | 4/2015 | Burkhart et al. |
| 9,107,653 B2 | 8/2015 | Sullivan |
| 9,521,999 B2 | 12/2016 | Dreyfuss |
| 2002/0052629 A1 | 5/2002 | Morgan |
| 2007/0060922 A1 | 3/2007 | Dreyfuss |
| 2009/0312776 A1 | 12/2009 | Kaiser |
| 2010/0152773 A1 | 6/2010 | Lunn |
| 2010/0249834 A1 | 9/2010 | Dreyfuss |

(Continued)

*Primary Examiner* — Shaun L David
(74) *Attorney, Agent, or Firm* — BLANK ROME LLP

(57) ABSTRACT

Systems and methods for soft tissue to bone repairs employing tensionable knotless anchors, without knot tying. The tensionable knotless anchors may be used by themselves or in combination with additional constructs (which may have a similar or different configuration, i.e., modified according to the specific repair) to achieve novel remplissage and soft tissue repairs.

25 Claims, 18 Drawing Sheets

(56) References Cited

U.S. PATENT DOCUMENTS

| | | |
|---|---|---|
| 2012/0130424 A1 | 5/2012 | Sengun |
| 2012/0179199 A1 | 7/2012 | Hernandez |
| 2013/0096611 A1 | 4/2013 | Sullivan |
| 2013/0165972 A1 | 6/2013 | Sullivan |
| 2013/0345749 A1 | 12/2013 | Sullivan et al. |
| 2014/0052179 A1 | 2/2014 | Dreyfuss |
| 2015/0272567 A1* | 10/2015 | Feezor ............... A61B 17/0485 606/232 |

* cited by examiner

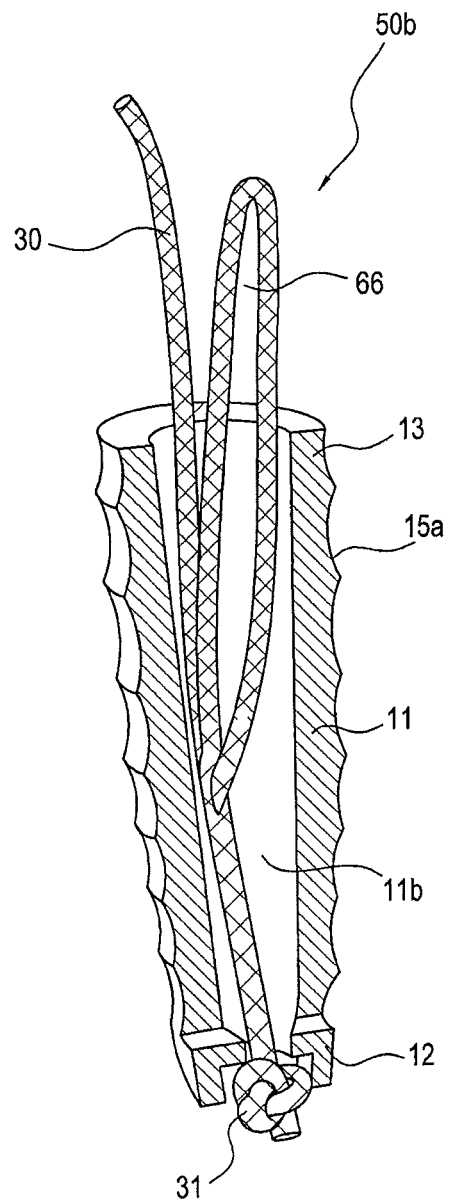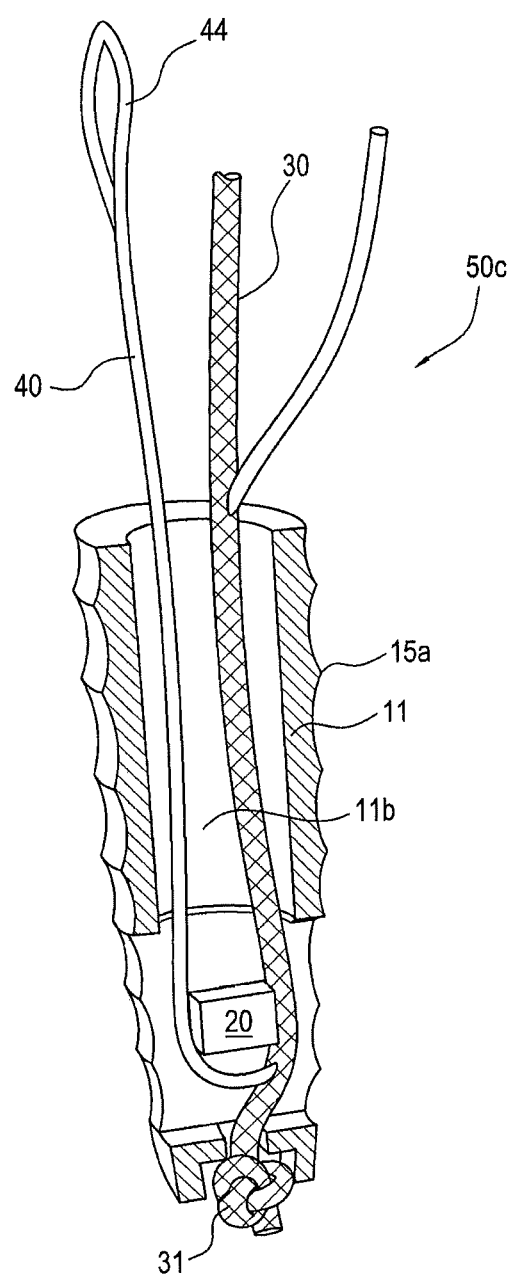
FIG. 3
FIG. 4

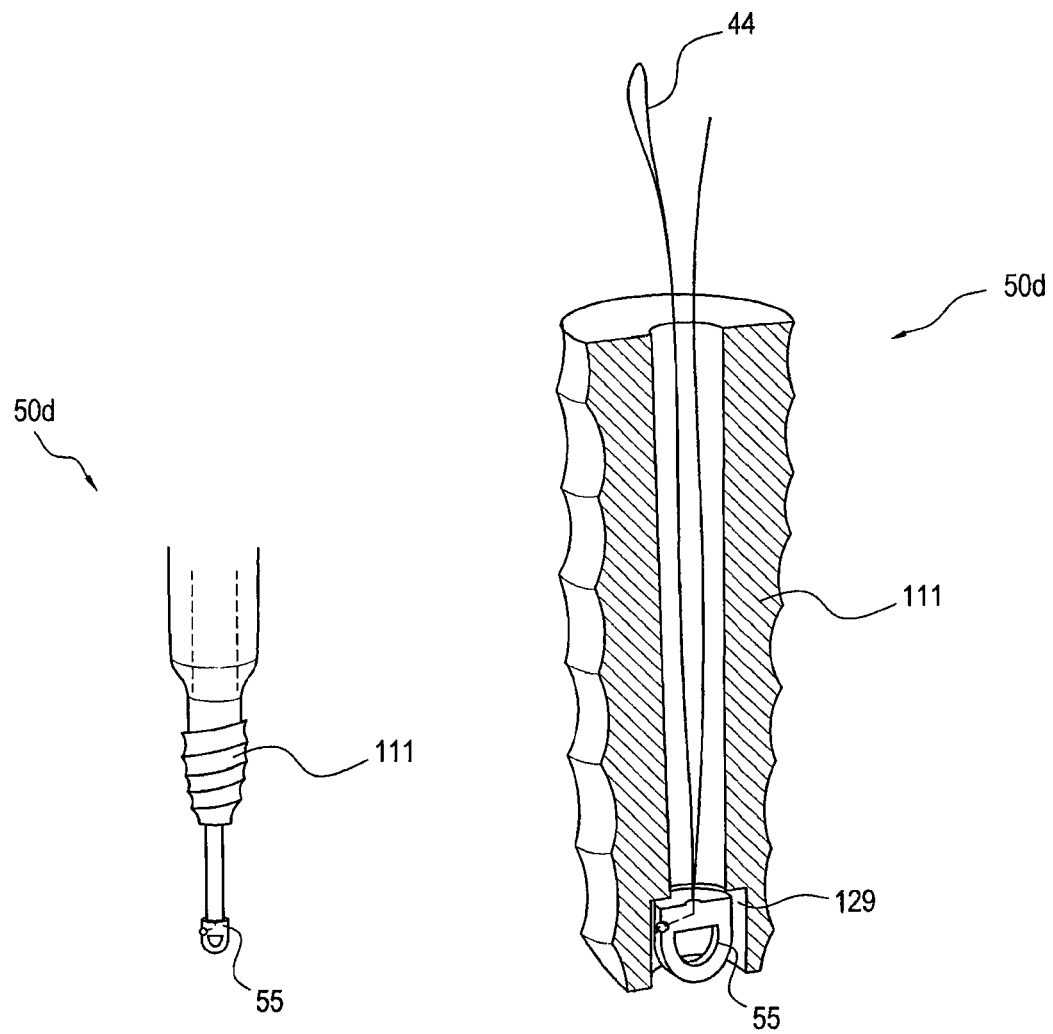

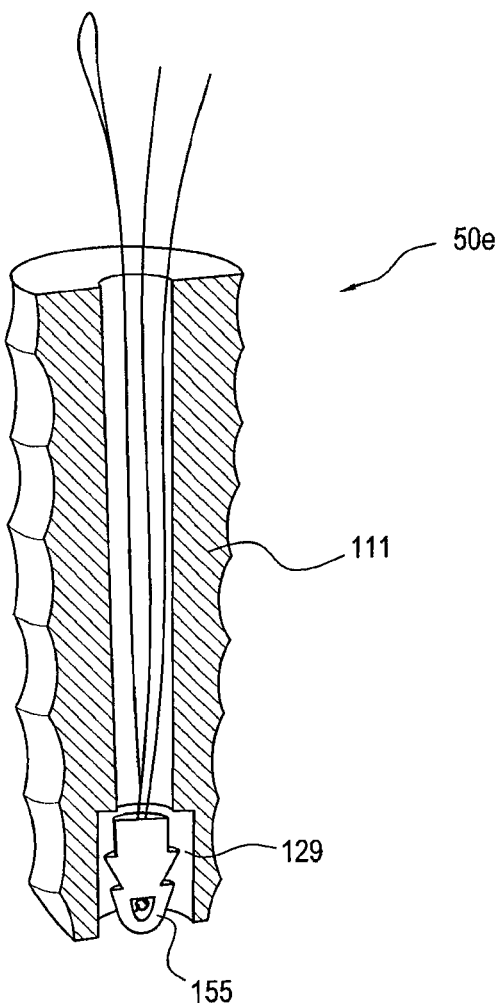
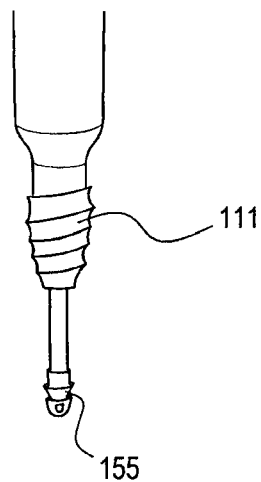
FIG. 7
FIG. 8

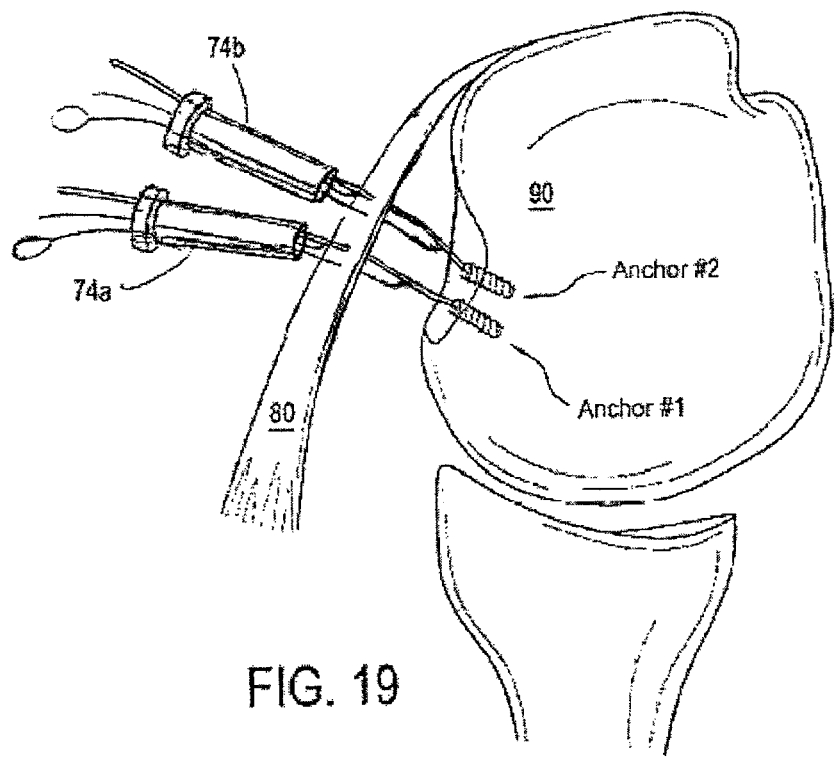
FIG. 19
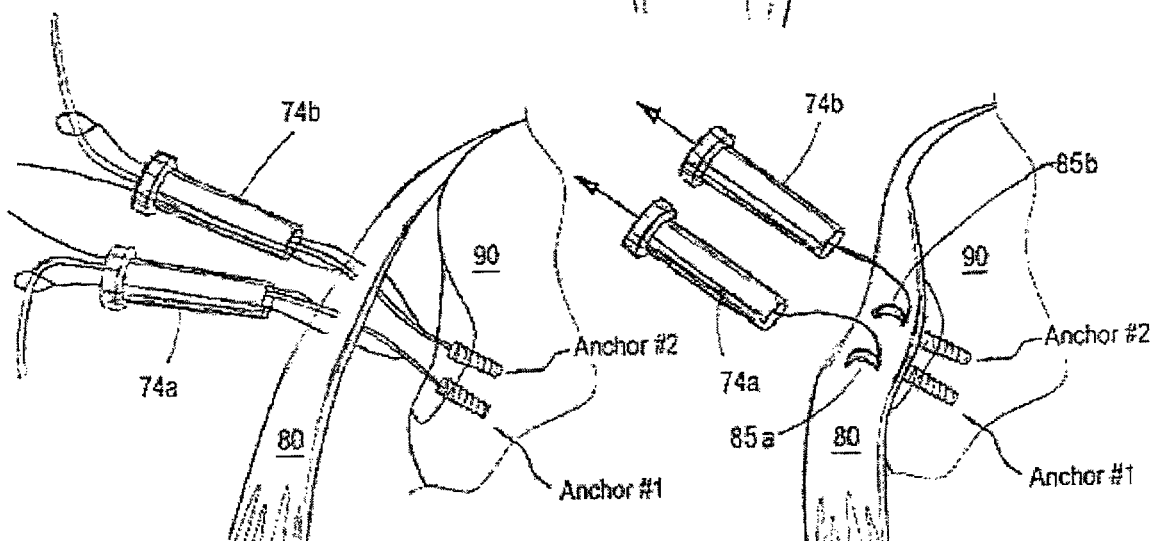
FIG. 20
FIG. 21

SURGICAL CONSTRUCTS AND METHODS OF TISSUE REPAIR

CROSS-REFERENCE TO RELATED APPLICATIONS

This is a continuation of application Ser. No. 16/419,801, filed May 22, 2019, now U.S. Pat. No. 11,439,382, which is a continuation of application Ser. No. 14/918,401, filed Oct. 20, 2015, now U.S. Pat. No. 10,368,855, the disclosures of which are incorporated by reference in their entireties herein.

BACKGROUND

The present invention relates to methods of tissue repair and surgical devices and, in particular, to suture constructs and associated methods of remplissage and tissue repairs.

SUMMARY

Knotted or knotless, tensionable fixation devices and methods of tissue repairs and remplissage techniques are disclosed.

Suture anchors provide significant stabilizing effect of bringing soft tissue into a bone defect and fixing soft tissue within the bone defect. Suture anchors allow for tensioning after insertion in bone defect (to allow attached tissue to be brought proximate to bone) and do not require tying of any knots.

BRIEF DESCRIPTION OF THE DRAWINGS

FIGS. 3 and 4 illustrate various views of a fixation device according to another exemplary embodiment.

FIGS. 5 and 6 illustrate various views of a fixation device according to another exemplary embodiment.

FIGS. 7 and 8 illustrate various views of a fixation device according to another exemplary embodiment.

FIGS. 19-21 illustrate another exemplary remplissage technique with fixation devices of FIGS. 1-10.

DETAILED DESCRIPTION

Figure 1A:
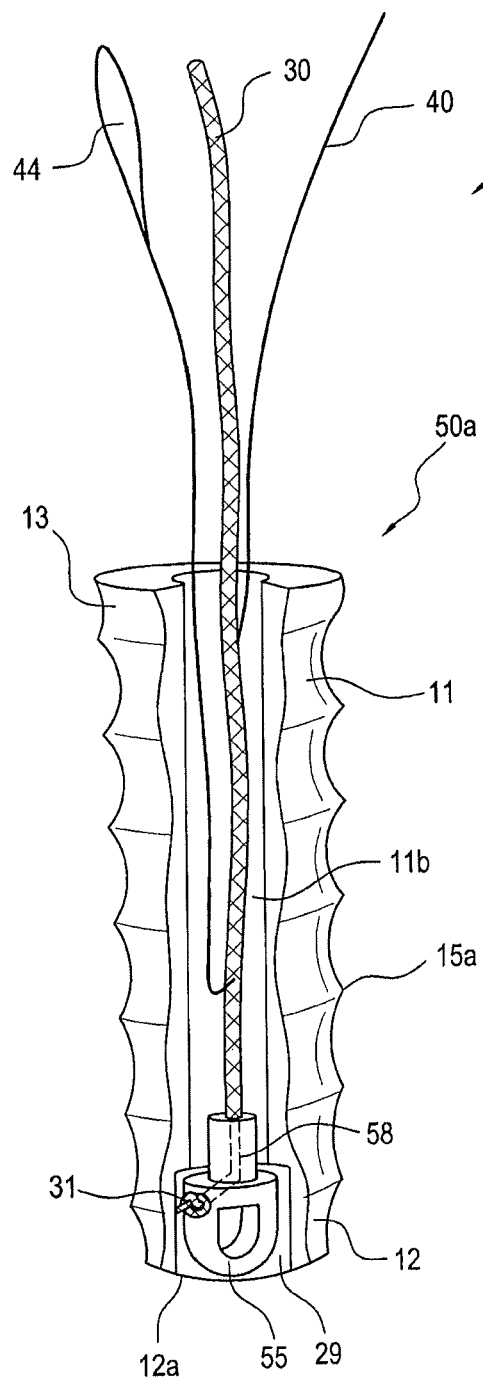
FIGS. 1a, 1b, and 2 illustrate various views of a fixation device according to an exemplary embodiment.

Surgical constructs, devices, systems, remplissage techniques, and soft tissue repairs such as transtendon repairs (for example, Partial Articular Surface Tendon Avulsion (PASTA) lesion repairs) or other knotless soft tissue repairs and fixations, such as fixation of soft tissue (ligament, tendon, graft, etc.) to bone, are disclosed. The knotless anchor constructs may be employed for any remplissage techniques such as Hill Sach's repairs and for any soft tissue repairs including PASTA, labral, rotator cuff, Achilles tendon, biceps and hip repairs, among many others.

The knotless suture constructs disclosed below use a mechanism similar to that of knotless SutureTak® but provide improvements in the design of the anchor constructs. As detailed below, novel anchor constructs in the form of (1) a combined knotless/knotted Corkscrew® anchor with a recessed eyelet; (2) a knotless Corkscrew® anchor; (3) a knotless SwiveLock® anchor with a recessed eyelet; and/or (4) a knotless PushLock® anchor may be used alone or in any combination to aid in suture management and tensioning.

Knotless suture anchors are provided for both PASTA and remplissage applications. These anchors have specific application to the humeral bone and have increased pullout strength.

The surgical devices (constructs) detailed below include fixation devices (tensionable knotless anchors) having various configurations that are inserted into a bone defect (such as a Hill Sach's lesion, for example) with a flexible strand (for example, a suture) provided within the fixation device and optionally a shuttle/pull device (a suture passing instrument) attached to the flexible strand. The flexible strand and the shuttle/pull device attached to it allow the formation of a splice within the body of the anchor, or outside the body of the anchor, and during the tissue repair procedure to finalize the construct. The shuttle/pull device is provided within the strand (inside of the strand) and forms the splice subsequent to the insertion of the fixation device within the bone (and subsequent to attachment to soft tissue to be repaired or fixated) to allow formation of the final fixation device with a knotless self-locking mechanism including a continuous, flexible loop having an adjustable perimeter that allows the user (for example, the surgeon) to control the tension of the strand on the soft tissue to be attached to bone.

Details of the formation of an exemplary knotless suture anchor employed in the embodiments of the present invention and with the splice- and loop-forming mechanism detailed above are set forth in U.S. Pat. No. 9,107,653, entitled "Tensionable Knotless Anchors with Splice and Methods of Tissue Repair," U.S. Patent Application Publication No. 2013/0165972, entitled "Tensionable Knotless Anchor Systems and Methods of Tissue Repair," and U.S. Patent Application Publication No. 2013/0345749, entitled "Knotless Suture Anchors and Methods of Tissue Repairs," the disclosures of all of which are incorporated by reference in their entirety herewith.

The present invention also provides remplissage techniques and methods of soft tissue repairs which do not require tying of knots and allow adjustment of both the tension of the suture and the location of the tissue with respect to the bone defect or lesion. In the exemplary methods detailed below with reference to FIGS. 1-25, the tensionable knotless anchors may be used by themselves or in combination with additional constructs (which may have a similar or different configuration, i.e., modified according to the specific repair) and with the flexible strand provided through tissue, around tissue, or through and around tissue to be fixated within the bone defect. The tensionable knotless anchors may be used to achieve simple stitch repairs, mattress stitch repairs or interlocked looped mattress repairs, among others, at the bone defect, preferably within the bone defect. The tensionable knotless anchors may be also provided in a daisy chain configuration, i.e., with the suture from one anchor passed through the eyelet/loop of the shuttle/pull device of another anchor and repeated in a pattern (to allow the formation of a splice within each anchor with a shuttle/pull device of another anchor).

The methods and devices (constructs) of the present invention will be detailed below with reference to exemplary knotless, self-cinching suture anchors 50a, 50b, 50c, 50d, 50e, 50f, 50g. Details of an anchor similar in part to knotless suture anchors 50a, 50b, 50c, 50d, 50e, 50f, 50g are set forth in U.S. Pat. No. 9,107,653 issued Aug. 18, 2015, entitled "Tensionable Knotless Anchors with Splice and Methods of Tissue Repair (the disclosure of which is incorporated in its entirety herewith), and are also provided in this application (for ease of understanding of the embodiments below), and with reference to FIGS. 26 and 27.

Figure 26:
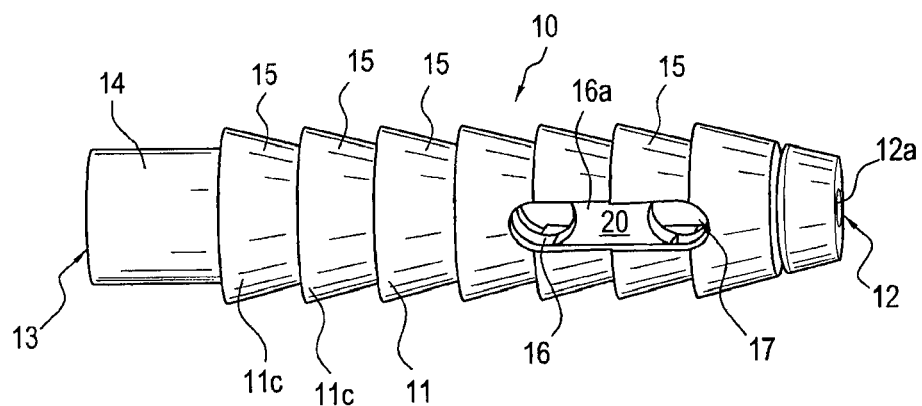
FIGS. 26 and 27 illustrate a side view and a cross-sectional view, respectively, of a tensionable knotless suture construct employed in exemplary methods of tissue repairs and remplissage techniques.
Figure 27:
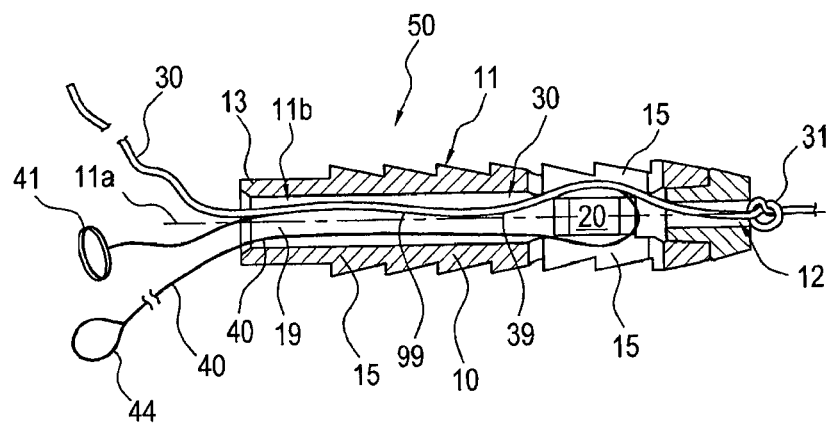

The tensionable, self-cinching knotless anchor 50 shown in FIGS. 26 and 27 has an anchor body 11 provided with a longitudinal axis 11a, a proximal end 13 and a distal end 12, and a plurality of ribs 15 extending circumferentially around it. Openings/channels 16 and 17 allow threading suture(s) and/or suture passing device(s) around post 20, as detailed below. Cannulation 11b extends along the body 11 to allow passage of flexible strands and of suture passing devices, as detailed below. Cylindrical portion 14 is provided at the proximal end 13 of the anchor 50 and contains a socket 19 (FIG. 27) configured to securely engage a tip of a driver. Openings/channels 16, 17 are positioned opposite to each other relative to the post 20 and also symmetrically located relative to the post 20, to allow flexible strand 30 (suture 30) and shuttle/pull device 40 (suture passing instrument 40 or shuttle 40) provided with eyelet or loop 44 to pass and slide therethrough.

Tensionable knotless anchor 50 is loaded with tensionable construct 99 formed of suture 30 attached to the shuttle/pull device 40. To assemble anchor 50, suture 30, which is typically braided or multi-filament, is preloaded onto the anchor by tying static knot 31, which prevents suture 30 from passing through distal blind hole 12a. The suture may also be preloaded by insert molding or by any other means known in the art. Suture 30 passes around post 20, which is large enough to allow suture 30 to take gradual turns instead of sharp turns. Suture 30 then passes through cannulation 11b and proximal blind hole 13a. Tensionable knotless anchor 50 is loaded onto a driver (not shown in FIGS. 26 and 27), and suture 30 is tied to the driver (for example, wrapped around a cleft of the driver) to fasten tensionable knotless anchor 50 securely to the driver.

Prior to the fastening of the anchor 50 to the driver, suture passing device 40 (for example, a FiberLink™ or a nitinol loop) is threaded through suture 30 (i.e., attached to the suture 30 through splice region 39), as shown in FIG. 27. Suture passing device 40 includes an eyelet/loop 44 for passing suture and, optionally, a pull-ring (not shown). Suture passing device 40 passes through an aperture of suture 30, located either proximal or distal to distal blind hole 12a. It then exits an aperture of suture 30, within the tensionable knotless anchor 50, traverses around post 20, and through proximal blind hole 13a. Tensionable knotless anchor 50 loaded with tensionable construct 99 (formed of suture 30 attached to the suture passing device 40) is then secured into bone (for example, into a hole/socket/tunnel formed in the bone) by using the driver. Suture 30 is then passed through or around the tissue which is to be reattached to bone. Suture 30 is subsequently passed through eyelet/loop 44 of the suture passing device 40. Suture passing device 40 is then pulled, thereby pulling suture 30 towards tensionable knotless anchor 50 so that it doubles on itself inside the body of the tensionable knotless anchor. The suture passing device 40 has also been further pulled through the splice region 38 of suture 30, to form a splice within the strand 30 and within the body of the anchor 50, and a continuous, flexible loop 55 (not shown) having an adjustable perimeter.

Anchor 50 may be a screw-in anchor or a push-in style anchor. Anchor 50 may be formed of metal, biocompatible plastic such as PEEK or a bioabsorbable material. Socket 19 at the distal end 13 of the anchor 50 is configured to securely engage a tip of a driver, as detailed below. The socket of the anchor 50 may have any shape adapted to receive a driver tip for tapping or screw-in style anchors. Tensionable knotless anchor 50 may be made of one or more pieces, or may be provided as an integrated device. As detailed below, the tensionable knotless anchor 50 may be modified to carry more than one suture/shuttle construct (i.e., more than a flexible strand 30 and a shuttle/pull device 40), or may be modified to carry no suture but only one or more shuttle/pull devices, etc. Furthermore, anchors with eyelets may carry one or more sutures or suture tapes inserted through the eyelet as desired by the surgeon.

Reference is now made to FIGS. 1-25 which illustrate various fixation devices (suture anchor constructs) and remplissage techniques and methods of attaching soft tissue to other tissue (such as bone) with such devices/constructs. For simplicity, the remplissage techniques have been grouped into four categories (techniques 1-4, or Embodiments A-D) set forth below.

Figure 1B:
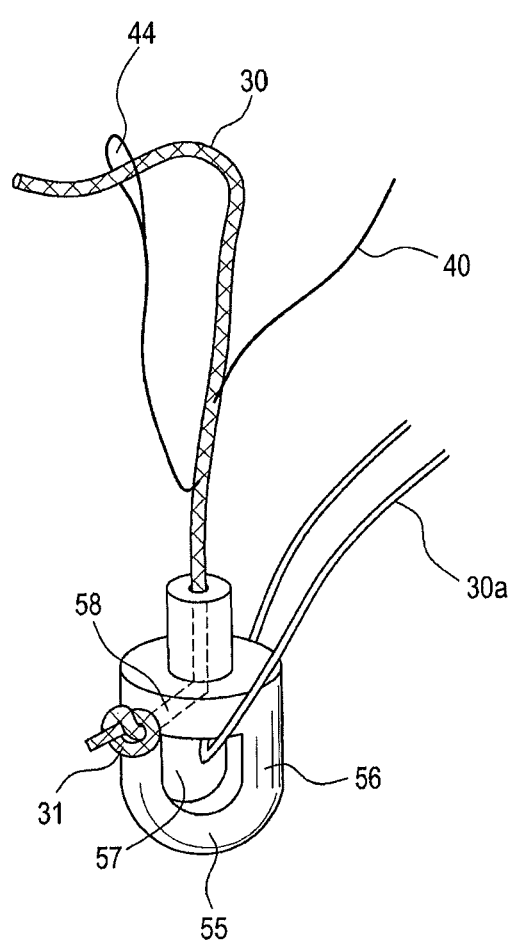
Figure 2:
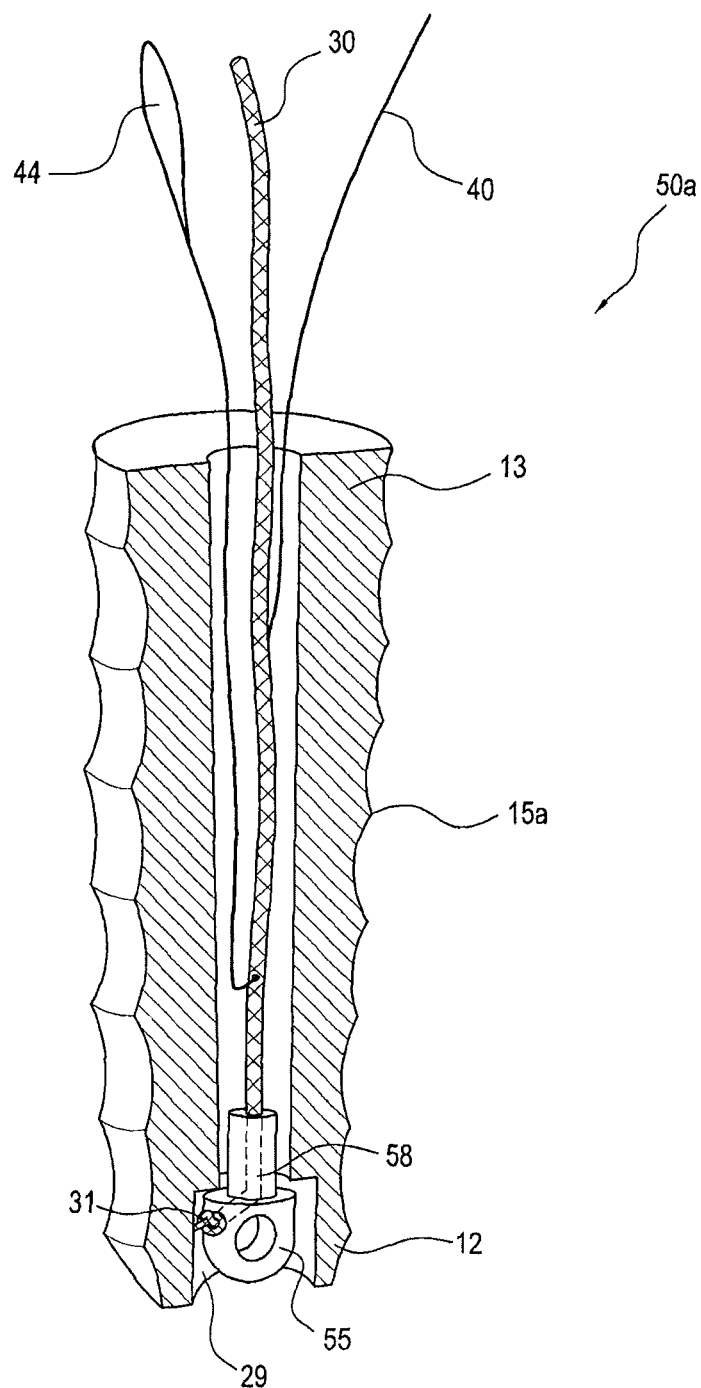

FIGS. 1a, 1b, and 2

FIGS. 1a, 1b, and 2 illustrate an exemplary surgical device comprising fixation device 50a in the form of a combined knotless/knotted Corkscrew® with a recessed eyelet 55, tensionable construct 99, and optionally sliding suture 30a. Fixation device 50a could be used for remplissage and for transtendon PASTA repairs. Flexible strand 30 and shuttling/pulling device 40 (suture passing instrument 40) that form knotless tensionable construct 99, as well as the formation of the splice and flexible, tensionable, self-cinching loop, are similar to those described above with respect to knotless anchor construct 50 of FIGS. 26 and 27.

Sliding suture 30a could be useful for surgeons that want to tie knots, or as a backup fixation if the knotless mechanism fails to function properly (e.g., if the suture 30 breaks or gets hung up when threading the splice, which sometimes happens during surgery) so that the anchor could still be used by tying a knot and would not have to be abandoned. One or more sliding sutures 30a could be provided. Exemplary combined knotless/knotted Corkscrew® 50a has a standard corkscrew fully-threaded profile with recessed PEEK eyelet 55 (eyelet and sutures are ghosted-in) and continuous threads 15a. PEEK eyelet 55 is housed within bore 29 provided at the most distal end 12 and in communication with cannulation 11b and with most distal surface 12a. Eyelet 55 may include eyelet body 56 with a through-hole or opening 57, which allows one or more flexible strands 30a (sliding sutures 30a) to slidingly pass therethrough. Eyelet 55 may also include eyelet channel/passage 58 through which flexible strand 30 of knotless tensionable construct 99 passes through. Eyelet channel 58 may be configured to extend to a hole on a surface of body 56 of the recessed eyelet where a static knot may be tied to secure tensionable construct 99. Alternatively, eyelet channel 58 may extend into opening 57 of eyelet 55, where a static knot is tied. In an exemplary embodiment illustrated in FIGS. 1a-2, flexible strand 30 of knotless tensionable construct 99 passing through eyelet channel/passage 58 is secured on the surface of eyelet 55 by tying a static knot 31.

The PEEK eyelet 55 recessed in tip of anchor body 11 (at most distal end 12 of anchor body 11) serves as anchor point for knotless rig, and also can accommodate a separate sliding suture 30a for knotted use (sliding suture 30a through eyelet 55 can be used to tie knot, if necessary, due to either: 1) surgeon's preference; or 2) back-up fixation in the event that the knotless mechanism fails to function properly).

Construct 50a may be inserted with a driver, such as a Corkscrew® driver, and could be inserted trans-tendon through an arthroscopic cannula, for example, a 5 mm cannula.

FIGS. 3 and 4

FIGS. 3 and 4 illustrate an exemplary surgical device using fixation device 50b in the form of a knotless Corkscrew® anchor. Fixation device 50b may be employed with a standard Corkscrew driver, and may be inserted through a 5 mm cannula that could be used for PASTA repairs (i.e., a 4.5 mm version of anchors 50b could pass through a 5 mm cannula). These fixation devices may be employed for knotless remplissage techniques with screw-in anchor options.

FIG. 3 illustrates knotless Corkscrew® 50b which may be formed of biocompatible, PEEK or metal material, and is provided with pre-threaded tensionable loop 66 formed within strand 30 that terminates in knot 31 at distal end 12. There is no internal post in this embodiment. This construct could be used with a standard Corkscrew® driver and could be inserted trans-tendon.

FIG. 4 illustrates knotless Corkscrew® 50c which may be formed of biocompatible, PEEK or metal material, and is provided with an internal post 20 and same threading mechanism as knotless SutureTak® 50 (FIGS. 26 and 27). This construct could be used with a standard Corkscrew® driver and, therefore, could be inserted trans-tendon through a 5 mm cannula (i.e., a 4.5 mm anchor 50c that would pass through a 5 mm cannula). Knotless Corkscrew® 50c could be made in 4.5 mm and 5.5 mm diameters, as well as 3 or 3.5 mm diameters.

As detailed below, knotless Corkscrew® 50c may be employed specifically for remplissage, wherein the surgeon is not just repairing the tissue back to bone but also is filling the bone defect with tendon so that the defect becomes extra-articular and prevents engagement and dislocation by means of a knotless interlocking suture anchor technique. With these constructs, remplissage techniques (particularly remplissage for off-track lesions) and PASTA repairs become much easier and reproducible than the remplissage and PASTA techniques currently known.

FIGS. 5-8

FIGS. 5-8 illustrate two embodiments a surgical device using fixation devices 50d, 50e in the form of knotless SwiveLock® anchors with recessed eyelet 55, 155 housed within bore 129.

A knotless SwiveLock® with a recessed eyelet shortens the length of the anchor by about 3 mm compared to the regular SwiveLock® (without a recessed eyelet). Construct 50d, 50e may be useful with acute insertion angles in PASTA repairs and remplissage. In fact, by taking a couple of threads off the anchor body 111, the anchor 111 becomes even shorter, as necessary in numerous surgical applications.

Preferably, the threaded sleeve 111 of the SwiveLock® inserter is narrower so that it could fit through a 5 mm cannula, which renders the SwiveLock® construct 50d, 50e even more versatile. A thick sleeve would be very difficult to use with the SwiveLock® for transtendon repairs.

Knotless SwiveLock® 50d with a Recessed Eyelet 55—First Embodiment

Knotless splice mechanism is external to eyelet 55. The threaded sleeve 111 is narrower so that it fits through a 5 mm cannula.

Knotless SwiveLock® 50e with a Recessed Eyelet 155—Second Embodiment

Knotless splice mechanism is internalized within the eyelet 155 (i.e., same mechanism as knotless SutureTak®).

The recessed eyelet 55, 155 may be useful in remplissage or PASTA repair by shortening the anchor length by 3 to 4 mm (compared to standard SwiveLock® where eyelet is external). With acute insertion angles, a shorter anchor is desirable.

Figure 9:
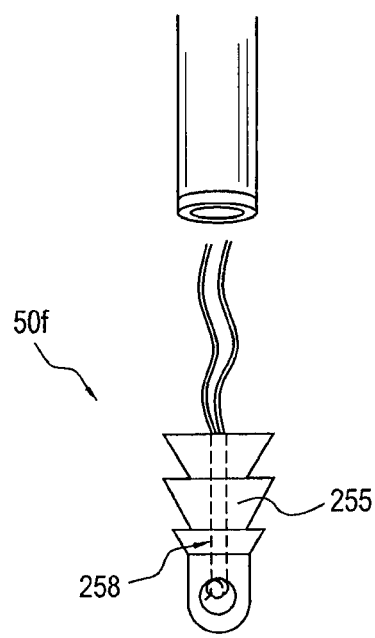
FIGS. 9 and 10 illustrate various views of a fixation device according to another exemplary embodiment.
Figure 10:
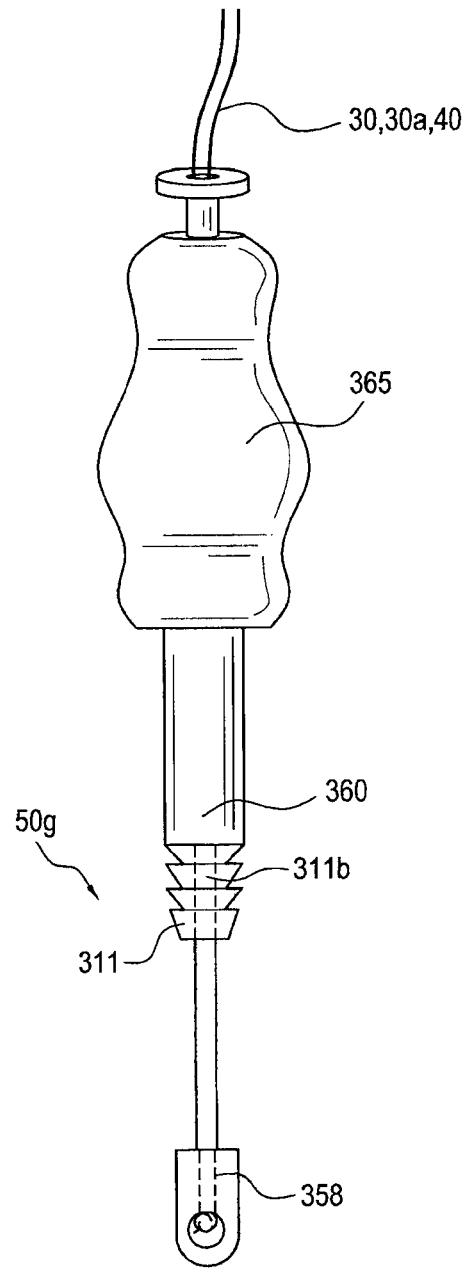

FIGS. 9 and 10

FIGS. 9 and 10 illustrate two embodiments of a surgical device using fixation devices 50f, 50g in the form of knotless PushLock® anchors with eyelet 255, 355. Eyelet 255, 355 may or may not be recessed, or may be partially recessed.

Unlike other PushLock® anchors, fixation devices 50f and 50g have a central cannulation for all accompanying flexible strands and sutures to pass through a fixation device body. For example, as shown in FIG. 10, flexible strand 30, shuttling/pulling device 40, and sliding suture 30a can all pass through central cannulation 311b of body 311. Additional flexible strands and sliding sutures can be used as desired by the surgeon. Since eyelet 255, 355 is secured by sutures, it does not require threaded attachment to a driver. Eyelet 255, 355 can also include a cannulation 258, 358.

Fixation devices 50f, 50g are advanced by impacting cylinder 360, rather than by being screwed in. Impacting cylinder 360 is cannulated to allow flexible strand 30, shuttling/pulling device 40, and sliding suture 30a to pass through the cannulation and exit out of handle 365.

Knotless PushLock® 50f with Eyelet 255—First Embodiment

Eyelet 255 is configured to have ridges, similar to eyelet 155 of fixation device 50e.

Knotless PushLock® 50g with Eyelet 355—Second Embodiment

Eyelet 355 is configured to be smooth, similar to eyelet 55 of fixation device 50d.

The above-described fixation devices 50a-50g can be used in remplissage techniques. In some ways, these constructs may be superior to the knotless SutureTak® for remplissage since their pull-out strength is greater, although the knotless SutureTak® may also be used for knotless remplissage techniques.

FIGS. 11-25 illustrate various exemplary embodiments of remplissage techniques and PASTA repairs as used with one or more exemplary fixation devices 50, 50a-50g, for example, fixation device 50d in the form of a knotless SwiveLock® with a recessed eyelet. With remplissage, the surgeon is not just repairing the tissue back to bone but the surgeon is also filling the bone defect with tendon so that the defect becomes extra-articular and prevents engagement and dislocation by means of a knotless interlocking suture anchor technique.

While the remplissage technique has been used for treating off-track lesions, the new techniques detailed below provide a novel, blind suture passage through a single cannula with knotless anchors. Biomechanical studies have demonstrated that there is a significant stabilizing effect of bringing the tendon into the bone defect and fixing it there.

Remplissage Technology: Embodiments A-D

The inventor of the present application has developed four distinct methods A, B, C, D of using the knotless SutureTak® device 50 and/or any of the fixation devices 50a-50g as an exemplary application. These methods are referenced as "remplissage" techniques and are described below. The remplissage procedure was initially described in 2007 by Wolf et al. as an adjunct to the arthroscopic anterior stabilization procedure of the shoulder in order to address a large engaging Hill-Sach's defect. The remplissage technique has been reported to be effective in reducing the incidence of recurrent anterior shoulder instability, when used along with arthroscopic Bankart repair.

The remplissage techniques detailed below may be used with threaded anchors such as fixation devices 50a-50g. The remplissage techniques detailed below may be also used with other devices, such as knotless Corkscrew®, PushLock®, and SwiveLock® anchors, among others. The techniques also find application in PASTA repairs.

The remplissage techniques detailed below fill the bone defect with tendon so that the defect becomes extra-articular and prevents engagement and dislocation by means of a knotless interlocking suture anchor. The surgeon employs a blind technique for doing this, without ever having to look up into the subacromial space.

The four remplissage techniques possess very unique and valuable features. The knotless suture anchors employed in such remplissage techniques may be used around any joint in the body, with the main application to remplissage of the shoulder.

Advantages:
1. Reduced surgical time (cutting surgical time by 75% in most cases).
2. Expands knotless SutureTak® anchors for other than arthroscopic labral repairs.
3. Lower patient risk (less time under anesthesia).
4. Interlocking of the knotless mechanisms between two anchors increases the loads to failure, providing a stronger construct.

Remplissage Technique 1—Embodiment A

Steps: The following narrative describes the application of the remplissage technique #1 for treating a Hill-Sach's defect 90 in vicinity of rotator cuff tendon 80.

Figure 11:
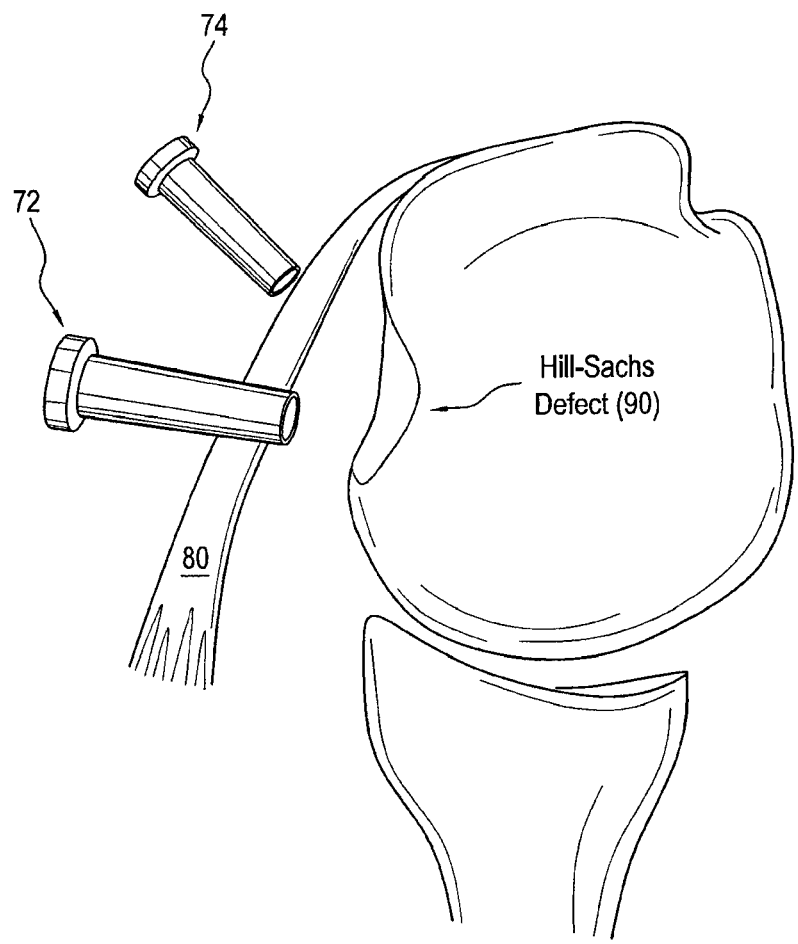
FIGS. 11-15 illustrate an exemplary remplissage technique with fixation devices of FIGS. 1-10.

Arthroscopic remplissage with anchor #1 and anchor #2, each provided with flexible strand 30 and shuttling/pulling device 40 with loop 44 (i.e., any of knotless SutureTak® anchor 50 and fixation devices 50a-50g detailed above).
1. Two cannulas 72, 74 are first put in place, an intra-articular cannula 72 for placement of anchors (fixation devices) and a sub acromial/sub deltoid cannula 74 for passing sutures (flexible strands), as shown in FIG. 11. The sub acromial/sub deltoid cannula 74 can toggle to allow penetration of various instruments such as a suture passer, and thereby the passage of suture (suture/Nitinol needle #1, and suture/Nitinol needle #2) into the tendon 80 at two different points or locations.

Figure 12:
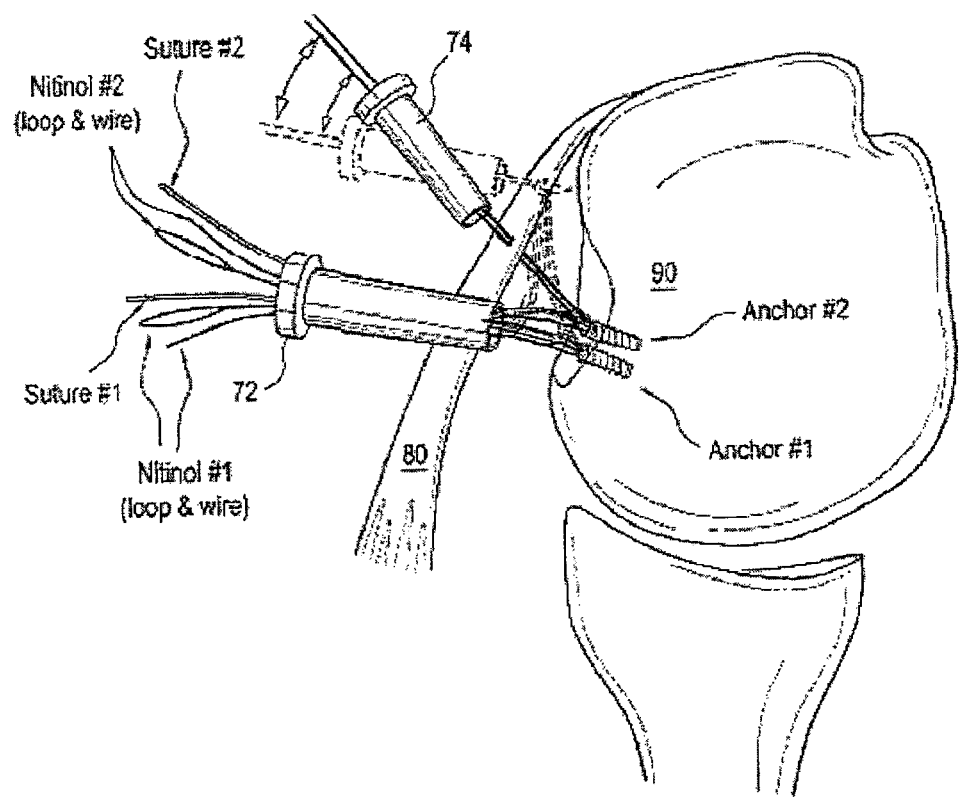

Two anchors (Anchor #1, Anchor #2) are then placed at the edge of the defect 90, through the intra-articular cannula 72, as shown in FIG. 12.

Figure 13:
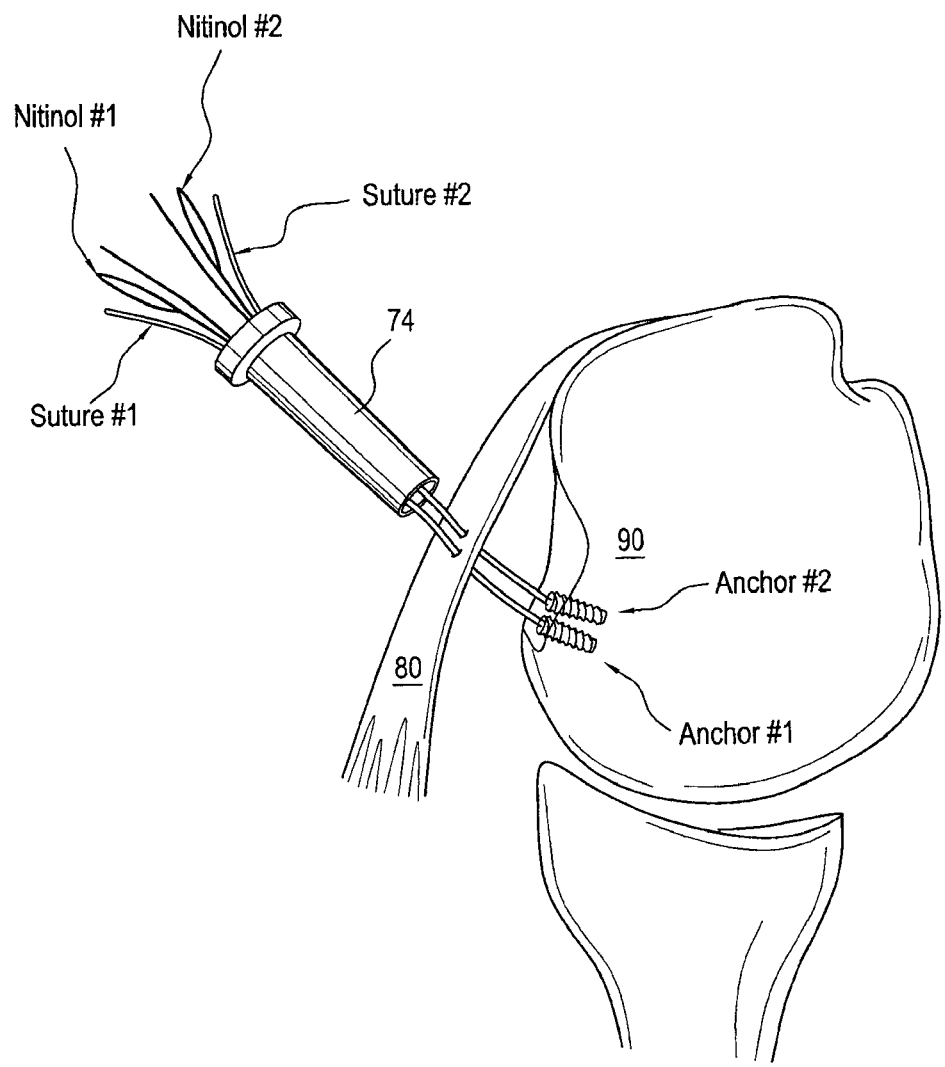
Figure 14:
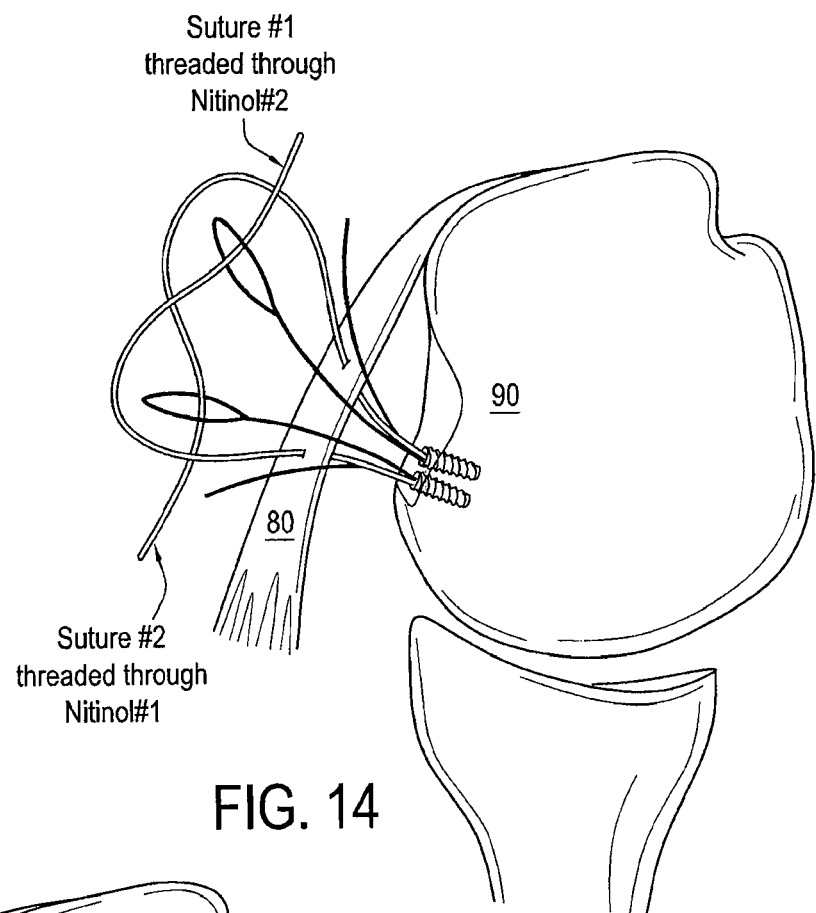
Figure 15:
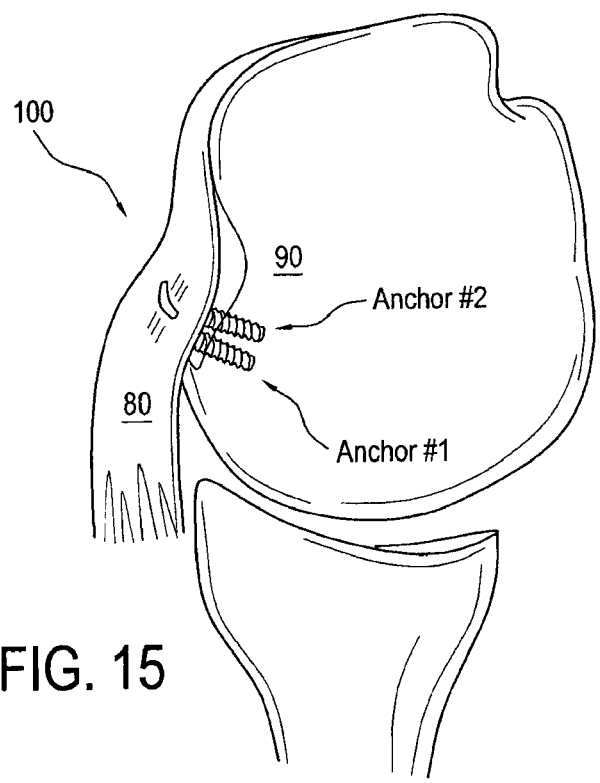

The sub acromial cannula 74 is then pushed against the tendon 80.
2. Retrieve each set of sutures through the sub acromial cannula 74; each set of sutures are to be retrieved through a separate point/location in the rotator cuff 80 while viewing from the intra-articular, as shown in FIG. 13.
3. Pass suture limb from one anchor through the splice of the other anchor by threading the suture through the Nitinol loop of the opposite anchor, then pulling reciprocally on the two free Nitinol limbs to bring the double loop down over the tendon bridge, as shown in FIG. 14.
4. The final construct/repair 100 is illustrated in FIG. 15. As illustrated, the double suture bridge serves to actively compress the tendon 80 into the Hill Sach's defect 90.

Note: The technique may also be adapted for use in the repair of a PASTA lesion with a double loop. Sutures may also be brought laterally to a third anchor where greater footprint compression is desired/clinically advisable. Additional anchors and/or fixation devices may be employed, if necessary and as required by each specific repair.

General Set-Up:
1. One posterior cannula (intra-articular) 72
2. One posterior-lateral cannula (subacromial) 74

Remplissage Technique 2—Embodiment B

Arthroscopic remplissage; this is a blind technique.

The technique unites the two anchor loops with an externally tied loop. The tensionable loops are pre-passed, meaning that the surgeon does not have to thread the splice in the two anchors, saving time as well as eliminating the possibility of malfunction with the splice passage.

Remplissage technique #2 may be used with various devices, including the knotless SutureTak®, knotless Corkscrew®, Pushlock® and/or SwiveLock® anchors.

Figure 16:
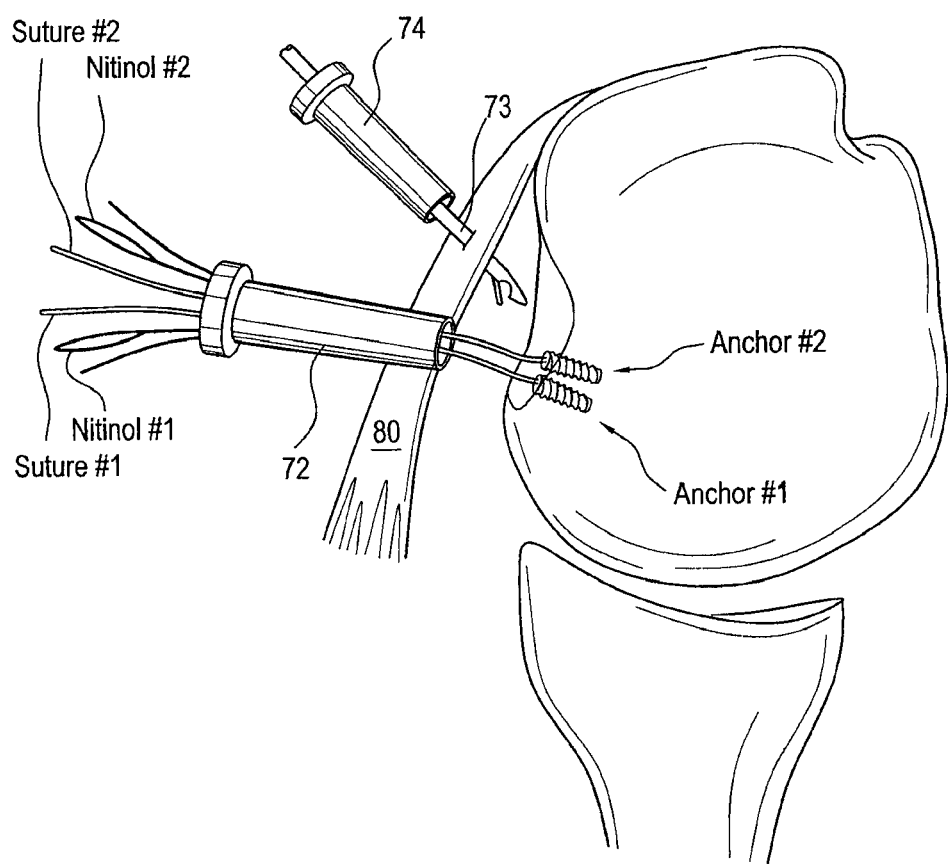
FIGS. 16-18 illustrate another exemplary remplissage technique with fixation devices of FIGS. 1-10.
Figure 17:
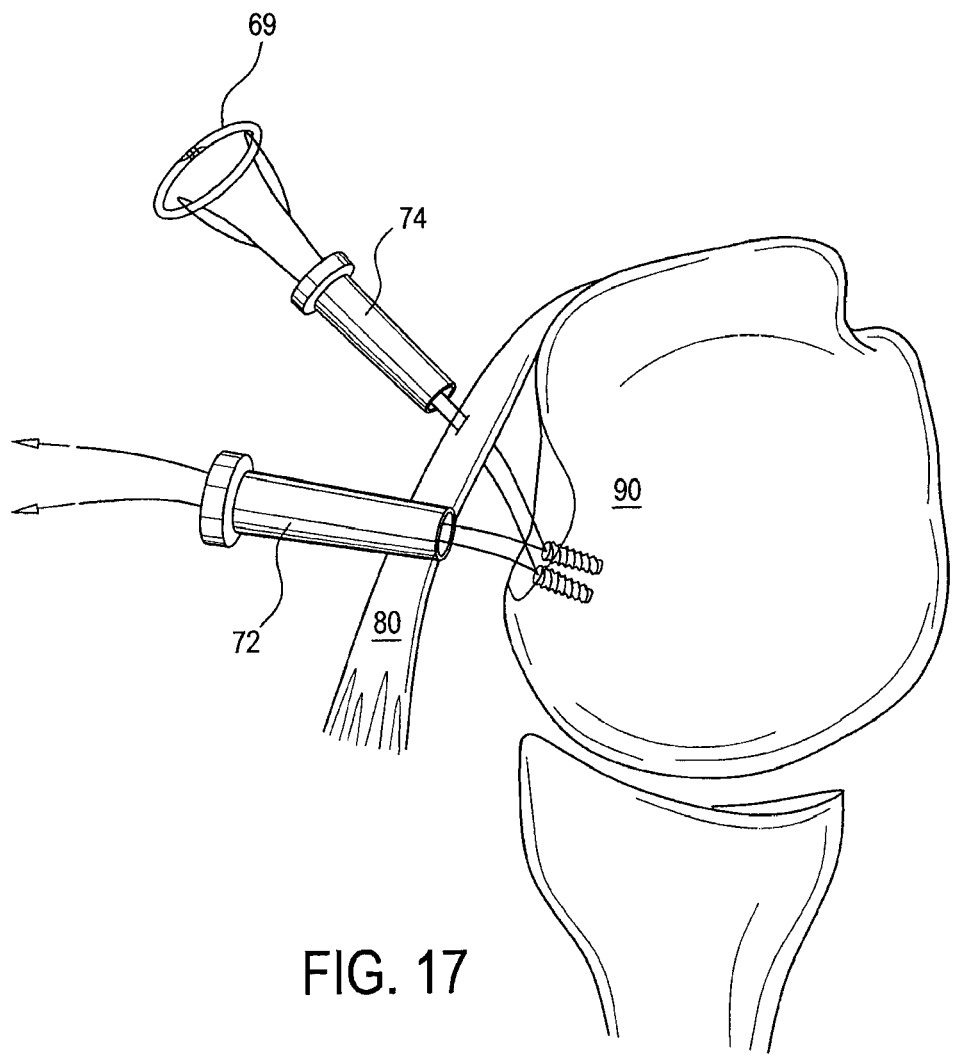
Figure 18:
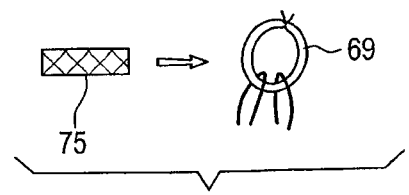

Steps: The following narrative describes the application of the remplissage technique #2 for repairing a Hill-Sach's defect 90.
1. Place two pre-looped knotless SutureTak® anchors or knotless Corkscrew® anchors (anchor #1, anchor #2) through a posterior portal and cannula 72. Intra-articular cannula 74 is illustrated penetrating the rotator cuff 80.
2. A separate sub acromial cannula 74 is also illustrated in FIG. 16, through which a suture passer 73 is inserted, and used to retrieve each loop through a separate trans-tendon puncture, as shown in FIG. 17.
3. Tie a separate loop of suture or suture-tape 69 (FIG. 18) between the two tensionable loops (tied outside the cannula 74). Note: It is recommended that the loop be tied over a 2 cm-circumference post. This will flatten to 1 cm over the cuff. The interposed loop is essential so that the tensioning limbs will not cause binding as the tensionable loops are pulled down. Consider using a 2 cm length of tape 75 (FIG. 18) with #2 suture leaders for tying, to provide broader compression.
4. Pull on the tensioning limbs to pull loop construct down on rotator cuff 80 to obtain a final repair (not shown).

Remplissage Technique 3—Embodiment C

The technique allows for creation of two separate knotless mattress stitches by a "blind" technique, in which the looped portion of the threading suture (the FiberLink® threader or suture passer 40 with loop 44) is separately passed so that a bridge of tendon is captured by the coreless loop as it enters back through the splice in the anchor. This remplissage technique may be used with the knotless SutureTak® (knotless Corkscrew®, PushLock® or SwiveLock®), or any of fixation devices 50a-50g.

The technique provides the creation of two separately-applied knotless mattress stitches 85a, 85b. FIGS. 19-21 schematically illustrate this third technique.

Steps: The following narrative describes the application of the remplissage technique #3.

1. Preplace two knotless SutureTak® or knotless Corkscrew® anchors, with FiberLoop® to thread the splice (FIG. 19). Two anchors (Anchor #1, Anchor #2) are then placed at the edge of the defect 90, through cannulas 74a, 74b as shown in FIG. 19.
2. Pass the sutures for the knotless mattress stitch, with each anchor providing a separate mattress stitch 85a, 85b through a separate cannula 74a, 74b (FIG. 20).
3. Coreless suture is passed over the tendon 80 via a separate puncture from Fiberlink®, providing a 1 cm tissue bridge between the puncture points for the mattress stitch 85a, 85b (FIG. 20—note the tensioning limb of the Fiberlink®; note the threading of the coreless suture through the looped end of the Fiberlink®).
4. Pull in direction A (FIG. 21) to tension the limbs of the Fiberlink® constructs to pull the tendon 80 to the bone defect 90 with two knotless mattress sutures or tape/suture composites (mattress stitches 85a, 85b).

Remplissage Technique 4—Embodiment D

Figure 22:
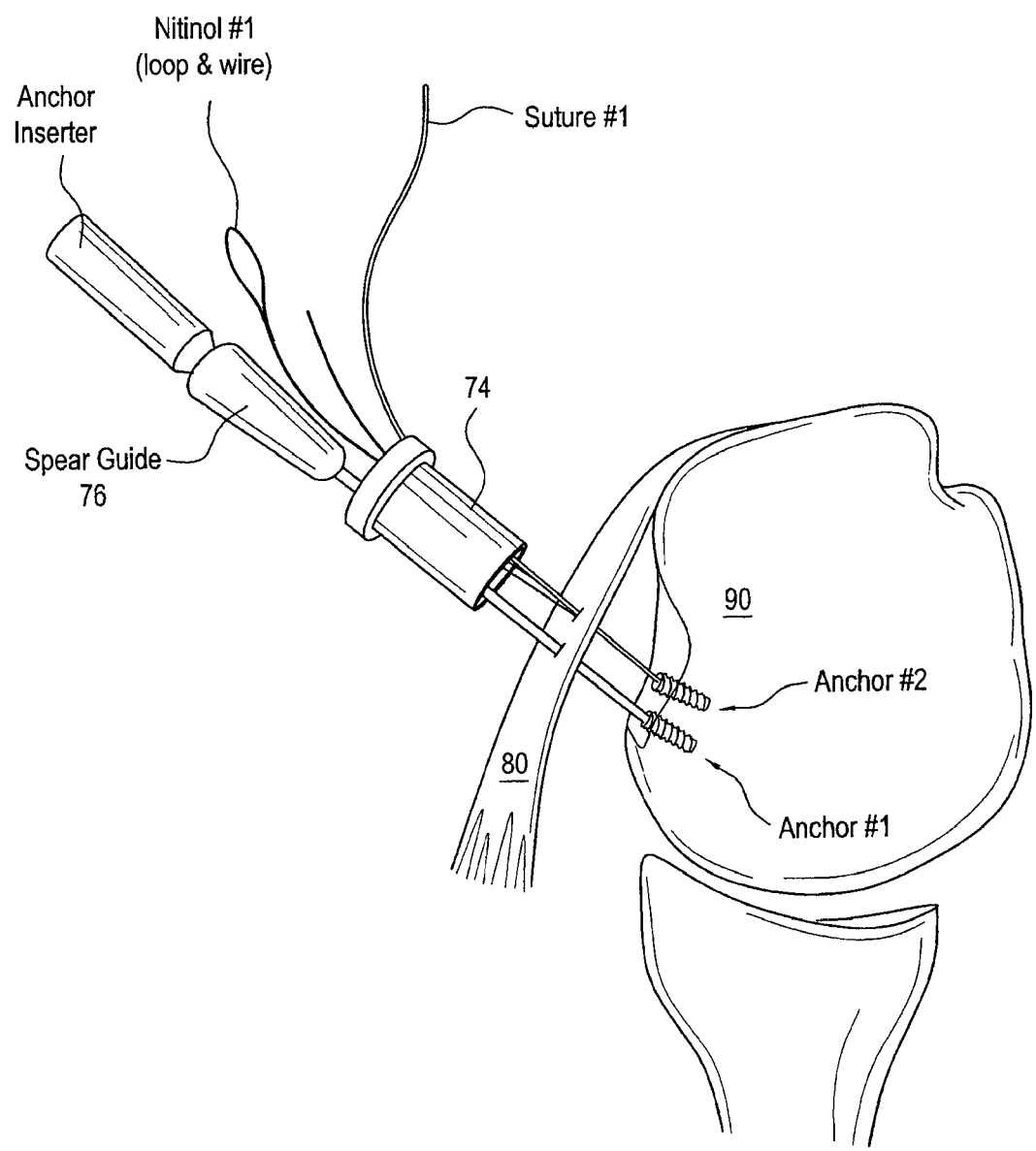
FIGS. 22-25 illustrate another exemplary remplissage technique with fixation devices of FIGS. 1-8.
Figure 23:
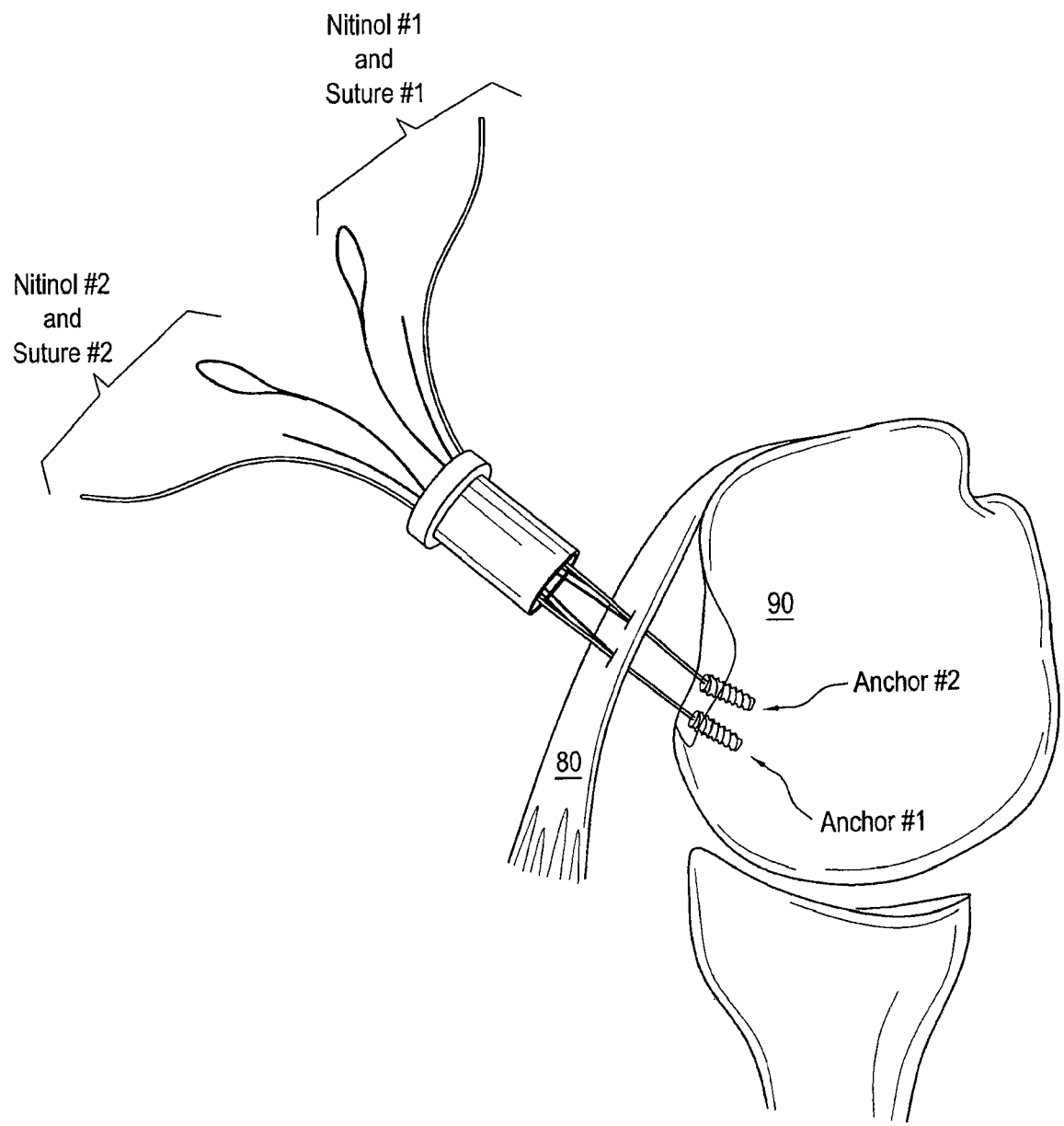
Figure 24:
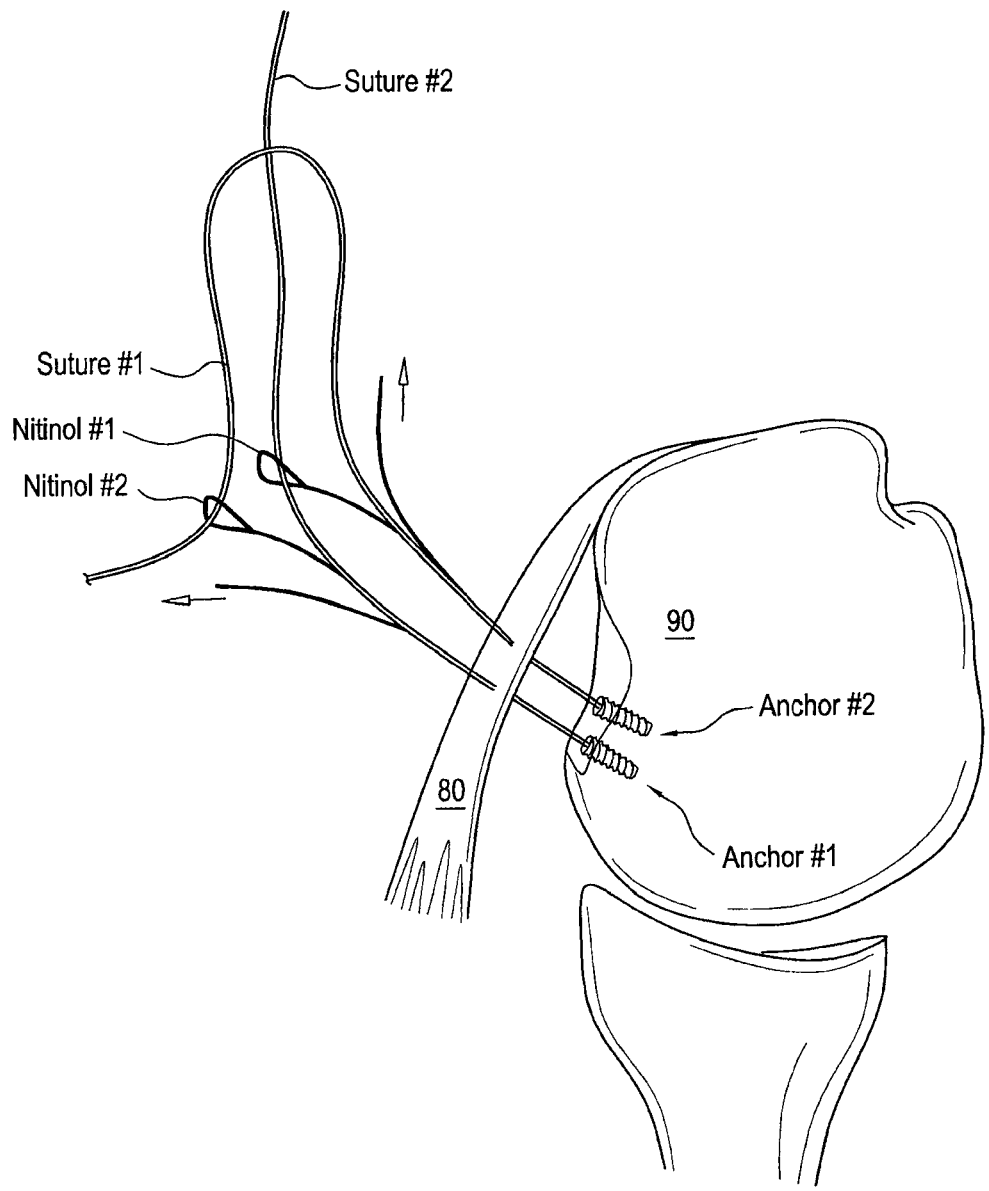
Figure 25:
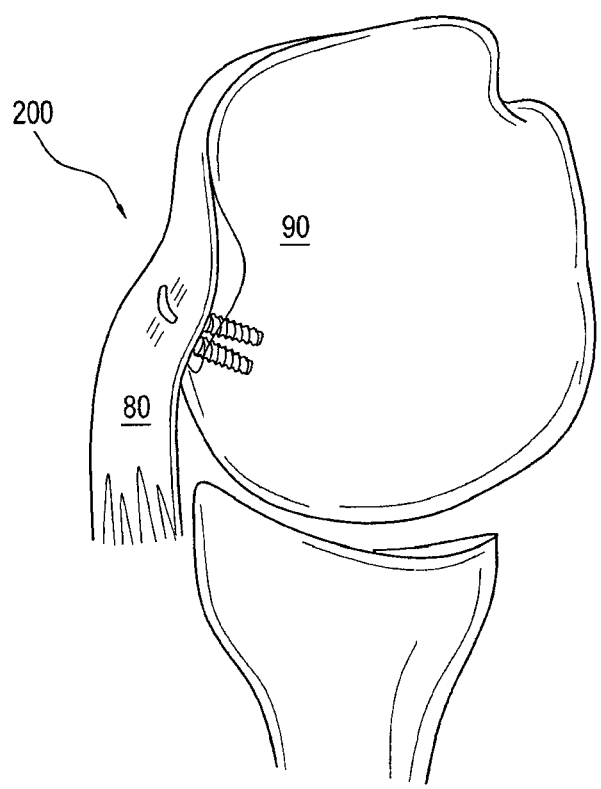

The technique allows for single-portal remplissage.
1. Subacromial cannula 74 is first put in place. Spear guide 76 passes through subacromial cannula 74, then penetrates tendon through the point that the surgeon wants to be opposed to bone, eliminating steps of passing suture through tendon after placing anchor in bone through a separate cannula. This is done for two separate anchors as shown in FIG. 22.
2. Remove inserter and guide (FIG. 23).
3. Thread suture from anchor #1 through nitinol loop from anchor #2. Thread suture from anchor #2 through nitinol loop from anchor #1. Then pull on tensioning limbs of nitinol wires to close the suture loops tightly down on the tendon, as shown in FIG. 24.
4. The final construct/repair 200 is illustrated in FIG. 25. Sutures have been tightened down into mattress configuration, insetting the tendon into the Hill-Sach's defect 90.

The present disclosure provides methods of stabilizing a bone or joint lesion, by inter alia (i) installing, through a first cannula, a plurality of fixation devices in a bone defect, each of the fixation devices including a flexible construct extending through the fixation device, the flexible construct comprising a flexible strand and a corresponding shuttling/pulling device attached to the flexible strand; (ii) passing, through a second cannula, each of the flexible strands through soft tissue to be fixated, at different locations within the soft tissue; (iii) passing each of the flexible strands through an eyelet of the shuttling/pulling devices; and (iv) pulling on each of the shuttling/pulling devices to allow each of the flexible strands to form a splice through itself and within the fixation device, and provide tensioning of the soft tissue to be fixated relative to the bone defect.

The bone defect may be a Hill-Sach's lesion. The bone defect may be a humeral head lesion, a femoral head lesion, a tibial head lesion, a distal tibial lesion, or a calcaneus lesion. The first cannula may be an intra-articular posterior cannula for placing the plurality of fixation devices, and the second cannula may be a subacromial, subdeltoid posterolateral cannula for passing the flexible strands.

A plurality of knotless closed loops may be formed, each having an adjustable perimeter. The plurality of knotless closed loops may be interlocked with each other by another loop formed of suture tape. Adjusting the perimeter of the knotless closed loops approximates the soft tissue to the bone defect. The soft tissue may be tendon, labrum, Achilles tendon, rotator cuff, biceps or capsular tissue. All steps may be conducted arthroscopically and without visualizing the subacromial space.

At least one of plurality of fixation devices can be an anchor with a fully-threaded body with a corkscrew profile, a cannulation, a proximal end, a distal end, and a recessed eyelet at the distal end, wherein the cannulation and the recessed eyelet are configured to allow the flexible strand and attached shuttling/pulling device to be passed through the body of the fixation device and through the recessed eyelet. The recessed eyelet is housed within a bore located at the distal end, the bore being in communication with the cannulation and with a most distal surface of the fully-threaded body. The shuttling/pulling device is configured to be pulled out of the body of the fixation device to allow the flexible strand to pass through itself and form a splice and a continuous, knotless, adjustable loop having an adjustable perimeter.

At least one of a plurality of fixation devices can alternatively be an anchor with a ridged body a cannulation, and an eyelet, and is impacted into place. The cannulation and the eyelet are configured to allow the flexible strand and attached shuttling/pulling device to be passed through the body of the fixation device and through the eyelet.

The present disclosure also provides a remplissage technique for a Hill-Sach's lesion by inter alia: (i) inserting a posterior, intra-articular cannula through skin and through a rotator cuff tendon located over a Hill-Sach's lesion; (ii) inserting at least one posterolateral subacromial cannula through skin and over the rotator cuff tendon; installing a plurality of fixation devices into the Hill-Sach's lesion, through the posterior, intra-articular cannula, each of the fixation devices including a flexible construct extending through the fixation device, the flexible construct including a flexible strand; (iii) passing, through the at least one posterolateral subacromial cannula, each of the flexible strands through the rotator cuff tendon, at different locations within the rotator cuff tendon; and (iv) fixating the rotator cuff tendon with the flexible strands within the Hill-Sach's lesion. The fixation devices may further include a corresponding shuttling/pulling device attached to the flexible strand.

The remplissage technique may further include the steps of: (v) passing each of the flexible strands through an eyelet of the shuttling/pulling devices; and (vi) pulling on each of the shuttling/pulling devices to allow each of the flexible strands to form a splice through itself and within the fixation device, and a continuous, knotless, self-cinching loop.

The flexible strands may be passed through the rotator cuff tendon to be fixated, and then through its corresponding eyelet of the shuttling/pulling device. The flexible strands may be passed through the rotator cuff tendon to be fixated, and then through an eyelet of a shuttling/pulling device of an adjacent fixation device. The flexible strands may be passed through the rotator cuff tendon to be fixated, and then through an eyelet of a different fixation device.

The remplissage technique may further include the steps of: installing a first and a second fixation devices into the Hill-Sach's lesion, each of the first and second fixation devices including a flexible construct extending through each of the first and second fixation devices, the flexible construct comprising a flexible strand and a corresponding shuttling/pulling device attached to the flexible strand; passing each of the flexible strands through the rotator cuff tendon adjacent the Hill-Sach's lesion; passing the flexible strand of the first fixation device through an eyelet of the shuttling/pulling device of the second fixation device, and passing the flexible strand of the second fixation device through an eyelet of the shuttling/pulling device of the first fixation device; and pulling on each of the shuttling/pulling devices to allow each of the flexible strands to form a splice through itself and within the fixation device, and provide tensioning of the rotator cuff tendon to be fixated within the Hill-Sach's lesion. At least one of the first and second fixation devices may be knotless anchor having a fully-threaded corkscrew configuration with a recessed eyelet provided at its most distal end.

The present disclosure also provides a remplissage technique for a Hill-Sach's lesion by inter alia: (i) inserting a subacromial cannula through skin and through a rotator cuff tendon located over a Hill-Sach's lesion; (ii) passing a spear guide through the subacromial cannula and penetrating the rotator cuff at a point opposed to bone; (iii) installing a plurality of fixation devices into the Hill-Sach's lesion, through the subacromial cannula, each of the fixation devices including a flexible construct extending through the fixation device, the flexible construct including a flexible strand; and (iv) fixating the rotator cuff tendon with the flexible strands within the Hill-Sach's lesion. Each fixation device may further include a corresponding shuttling/pulling device attached to the flexible strand.

The remplissage technique may further include the steps of: (v) passing the flexible strand of the first fixation device through an eyelet of the shuttling/pulling device of the second fixation device, and passing the flexible strand of the second fixation device through an eyelet of the shuttling/pulling device of the first fixation device; and (vi) pulling on each of the shuttling/pulling devices to allow each of the flexible strands to form a splice through itself and within the fixation device, and provide tensioning of the rotator cuff tendon to be fixated within the Hill-Sach's lesion.

The knotless suture constructs and systems of the present invention are used in conjunction with any knotless fixation devices which can allow a flexible strand and attached suture passing device to form a splice within the body of the fixation device. The fixation devices may be any of swivel and/or screw-in suture anchors and/or push-in suture anchors (such as an Arthrex SwiveLock® anchor, disclosed in U.S. Pat. No. 9,005,246, or a PushLock® anchor, as disclosed in U.S. Pat. No. 7,329,272, the disclosures of which are incorporated by reference in their entirety herewith). The fixation devices may be also any anchors, implants or screws (such as interference screws or tenodesis screws) or any fixation element that allows attachment/fixation of the knotless suture construct to bone during the remplissage techniques described above. The fixation devices/implants may have various sizes (various diameters and/or lengths) and may be formed of biocompatible materials such as PEEK, biocomposite materials, metals and/or metal alloys, or combination of such materials, among others.

The flexible strand 30 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. Typically the suture will be UHWMPE suture without a core to permit ease of splicing. The shuttle/pull device may be a shuttle/pull suture device such as a FiberLink® or a Nitinol loop.

The strands may also be formed of a stiff material, or combination of stiff and flexible materials, depending on the intended application. The strands may be also formed of suture tape or a combination of suture and tape, a stiff material, or combination of stiff and flexible materials, depending on the intended application. The strands may also have a cross-sectional shape that transitions from round (in the case of a suture) to flat (in the case of a suture-tape). The strands may be also coated and/or provided in different colors. The knotless anchors of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Pat. Nos. 8,439,976 and 8,460,379, the disclosures of which are incorporated by reference in their entirety herein.

What is claimed is:

1. A device for tissue repairs, comprising:
    an anchor body that is cannulated and that comprises an outer surface having a fixation structure for securing the anchor body in a bone hole;
    a one-piece tip that is separable from the anchor body, the tip comprising a proximal first portion that is insertable into an opening at a distal end of the anchor body and a distal tip body that defines a recess configured to hold a flexible material, wherein at least part of the first portion is cylindrical to facilitate rotation of the tip relative to the anchor body when the first portion is inserted, wherein at least part of the recess is located distal to the entire cylindrical part of the first portion; and
    a tensionable construct extending from the first portion of the tip into the anchor body, the tensionable construct comprising a flexible strand defining two apertures at different locations along a length of the flexible strand, and a passage extending through the flexible strand and connecting the two apertures, for forming a splice and a loop with an adjustable perimeter adjacent the splice.

2. The device of claim 1, wherein the cylindrical part of the first portion of the tip defines a greatest width of the first portion of the tip to facilitate the rotation of the tip relative to the anchor body when the first portion is inserted.

3. The device of claim 1, wherein a width of the tip body is greater than a greatest width of the first portion of the tip.

4. The device of claim 3, wherein the first portion of the tip is cannulated and defines a passage that extends into the tip body.

5. The device of claim 3, wherein the recess forms an eyelet that extends transversely through the tip body.

6. The device of claim 1, wherein the flexible strand of the tensionable construct further comprises the splice formed at the passage and the loop, and wherein the loop is a knotless, tensionable, self-cinching loop with the adjustable perimeter.

7. The device of claim 1, wherein the tensionable construct further comprises a knot and a free end.

8. The device of claim 1, wherein the passage forms a coreless portion of the flexible strand.

9. The device of claim 1, further comprising the flexible material that is separate from the tensionable construct, wherein the flexible material is releasably held in the recess.

10. The device of claim 1, wherein the tip is insertable into the anchor body such that the entire recess of the tip is located inside the anchor body.

11. The device of claim 1, wherein the tip further comprises a solid portion formed along a longitudinal axis of the tip that separates the recess from a proximal end of the tip.

12. The device of claim 1, wherein the tensionable construct is separated entirely from the recess.

13. A device for tissue repairs, comprising:
an anchor body that is cannulated and that comprises an outer surface having a fixation structure for securing the anchor body in a bone hole;
a tip that is separable from the anchor body, wherein the tip defines a recess configured to hold a flexible material and comprises a proximal first portion that is insertable into an opening at a distal end of the anchor body; and
a tensionable construct extending from the first portion of the tip into the anchor body, the tensionable construct comprising a flexible strand defining two apertures at different locations along a length of the flexible strand, and a passage extending through the flexible strand and connecting the two apertures, for forming a splice and a loop with an adjustable perimeter adjacent the splice;
wherein the flexible material is separate from the tensionable construct; and
wherein the tensionable construct is fixedly connected to the tip while the flexible material remains slidably held in the recess, with a first segment of the tensionable construct extending distally along a first direction from the first portion of the tip towards a distal end of the tip and a second segment of the tensionable construct extending away from a distal end of the first segment along a second direction different from the first direction.

14. The device of claim 13, wherein the first and second segments of the tensionable construct are directly connected to one another with the second segment angled around part of the tip relative to the first portion.

15. The device of claim 13, wherein the second segment of the tensionable construct extends laterally through the tip to an opening on an outer side surface of the tip.

16. The device of claim 13, wherein the tip further comprises a solid portion formed along a longitudinal axis of the tip that separates the recess from a proximal end of the tip.

17. The device of claim 13, wherein the tip further comprises a tip body that is distal to the first portion of the tip and that defines the recess, and wherein a width of the tip body is greater than a greatest width of the first portion of the tip.

18. The device of claim 17, wherein the first portion of the tip is cannulated and defines a passage that extends into the tip body.

19. The device of claim 13, wherein the tensionable construct further comprises a knot and a free end.

20. The device of claim 13, wherein the passage forms a coreless portion of the flexible strand.

21. A device for tissue repairs, comprising:
an anchor body that is cannulated and that comprises an outer surface having a fixation structure for securing the anchor body in a bone hole;
a tip that is separable from the anchor body, wherein the tip defines a recess comprising a proximal first portion that is insertable into an opening at a distal end of the anchor body; and
a tensionable construct extending from the first portion of the tip into the anchor body, the tensionable construct comprising a flexible strand defining two apertures at different locations along a length of the flexible strand, and a passage extending through the flexible strand and connecting the two apertures, for forming a splice and a loop with an adjustable perimeter adjacent the splice;
wherein the tensionable construct is fixedly connected to the tip without extending through any distally facing opening on the tip while the recess remains substantially unobstructed to slidably hold a flexible material that is separate from the tensionable construct.

22. The device of claim 21, wherein part of the tensionable construct extends laterally through the tip to an opening on an outer side surface of the tip.

23. The device of claim 21, wherein the tip further comprises a tip body that is distal to the first portion of the tip and that defines the recess, and wherein a width of the tip body is greater than a greatest width of the first portion of the tip.

24. The device of claim 21, wherein the tensionable construct further comprises a knot and a free end.

25. The device of claim 21, wherein the passage forms a coreless portion of the flexible strand.

* * * * *